United States Patent [19]

Yamada

[11] Patent Number: 5,122,521
[45] Date of Patent: Jun. 16, 1992

[54] STEROL COMPOUND
[75] Inventor: Yasuji Yamada, Tokyo, Japan
[73] Assignee: Taisho Pharmaceutical Co., Ltd., Japan
[21] Appl. No.: 729,343
[22] Filed: Jul. 12, 1991
[30] Foreign Application Priority Data
  Jul. 17, 1990 [JP] Japan .................... 2-188614
[51] Int. Cl.$^5$ .................... A61K 31/58; C07J 17/00
[52] U.S. Cl. .................... 514/172; 540/94
[58] Field of Search .................... 540/94; 514/173, 172
[56] References Cited
U.S. PATENT DOCUMENTS
  2,915,433 12/1959 Agnello et al. .................... 514/172
  2,915,435 12/1959 Agnello et al. .................... 514/172
  3,137,712 6/1964 Birkenmeyer et al. .................... 260/397.45

FOREIGN PATENT DOCUMENTS
  61620 9/1967 Japan .................... 514/172

Primary Examiner—Werren B. Lone
Assistant Examiner—Kimberly J. Kestler
Attorney, Agent, or Firm—Lorusso & Loud

[57] ABSTRACT

A novel sterol compound having an antitumor activity is disclosed. The compound is prepared by extracting sponges of the genus Xestospongia with an organic solvent and purifying the extract by conventional methods.

2 Claims, No Drawings

STEROL COMPOUND

BACKGROUND OF THE INVENTION

1. Field of the Invention

This invention relates to a novel sterol compound which possesses an antitumor activity.

2. Description of the Prior Art

Heretofore there is no report on sterol compounds which have chemical structure similar to the present compound and exhibit antitumor activity.

SUMMARY OF THE INVENTION

Sponges of the genus *Xestospongia* occur at coral reefs off Iriomote-jima Island of Okinawa Prefecture, Japan. We have found that extract from sponges of the genus *Xestospongia* contains a novel sterol compound which has an antitumor activity. This invention has been completed on the basis of the finding.

It is an object of the invention to provide a novel sterol having an antitumor activity and a process for preparing thereof.

It is another object of the invention to provide an antitumor pharmaceutical composition comprising the sterol.

DETAILED DESCRIPTION OF THE INVENTION

The sterol compound of the invention can be represented by the formula I

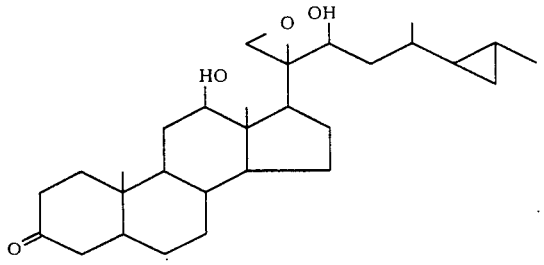

The compound of the invention represented by the formula I is isolated from natural sponges of the genus *Xestospongia*, which are extracted with an organic solvent followed by fractionation and purification of the content of said extract according to conventional techniques. The organic solvent employed includes, for example, methanol, ethanol, ether, acetone, benzene, toluene and ethyl acetate. Other appropriate solvents may also be used. The fractionation and purification are accomplished, for example, by chromatographic technique such as column chromatography on silica gel, preparative silica gel thin layer chromatography or high-performance liquid chromatography, or by recrystallization. Eluents herein used include ether, petroleum ether, n-hexane, ethyl acetate, benzene, toluene, acetone. methanol, ethanol, chloroform or dichloromethane. Those eluents may be used either alone or blended with each other.

The sterol thus obtained has remarkable antitumor activity and can be used as an antitumor agent for mammals including human being. For the purpose, the compound can be administered and suppositories, which can all be prepared according to conventional means.

The dosage of the compound depends on age, body weight and response of the patient, the route of administration and orally or parenterally at a dosage level in a range between 10 to 500 mg per day in an adult (about 0.1 to 10 mg/kg of body weight), if necessary, divided into one to three doses. The dose will vary depending upon conditions of diseases and the route of administration.

The compound is formulated either alone or in admixture with pharmaceutical carriers or excipients by a conventional method into tablets, capsules, injectable solutions, suspensions and suppositories, which can all be prepared according to conventional means. The carriers or excipients include calcium carbonate, starch. sucrose, lactose, talc, magnesium stearate and the like.

EXAMPLE

The invention will be explained in more detail below with reference to an example.

Example

Sponges of the genus *Xestospongia* were collected at coral reefs off Iriomote-jima Island of Okinawa Prefecture, Japan and immediately frozen with dry ice. The frozen material (3.1 kg) was impregnated with cold methanol (6 lit.) overnight. The methanol extract was filtered, and the filtrate was concentrated under reduced pressure to obtain 87.4 g of a residue. Additional methanol extractions were twice carried out in the same way as above to afford 50 g of an extract. The methanol extracts (137.4 g) were combined and suspended in 1.5 lit. of water. The aqueous suspension was extracted three times with 1.5 lit. of ethyl acetate. Combined ethyl acetate extracts were concentrated under reduced pressure to give 26.0 g of an ethyl acetate-soluble product. The ethyl acetate-soluble product (21 g) was subjected to column chromatography on silica gel (Fuji-Davison BW-820 MH, 500 g). There were produced five fractions (Fraction 1 eluted with 1000 ml of hexane, fraction 2 eluted with 1000 ml of hexane:ethyl acetate=2:1, fraction 3 eluted with 1000 ml of hexane:ethyl acetate=1:2, fraction 4 eluted with 1000 ml of ethyl acetate and fraction 5 eluted with 1500 ml of methanol). The fraction 4 (6.56 g) thus obtained was further subjected to column chromatography on silica gel (Fuji-Davison BW-820 MH, 150 g, eluted with hexane:ethyl acetate=1:1, one fraction was of 40 ml. There were produced 25 fractions. Fractions 13-20 (2.91 g) were subjected to flash chromatography (Silicagel, Fuji-Davison BW-300, 200 g, eluent, hexane:ethyl acetate=2:1, one fraction was of 40 ml). There were produced 66 fractions. Fractions 41-47 (460 mg) produced crystals which were then recrystallized from hexane-ethyl acetate to yield 233 mg of the present compound as colorless needles.

m.p.: 157°-158° C.

Elementary analysis: Calc'd.(%) C: 75.94, H: 10.11. Found (%) C: 75.64, H: 10.20.

IR(KBr) cm$^{-1}$: 3490, 3394, 1708, 1030.

$^1$H-NMR (500 MHz, CDCl$_3$) δ(ppm): 0.16(1H, q, J=4.5 Hz), 0.26(2H, m), 0.50(1H, heptet, J=5.9 Hz), 0.73(3H, s), 0.83(1H, m), 0.91(1H, m), 0.95(3H), 0.96(1H, m), 1.01(3H, s), 1.02(3H, d, J=6.1 Hz), 1.07(1H, dd, J=7.8 Hz, 11.0 Hz), 1.45(1H, m), 1.50(1H, m), 1.62(1H, m), 1.71(1H, qd, J=3.1 Hz, 13.1 Hz), 1.75(1H, m), 1.79(1H, td, J=4.2 Hz, 13.0 Hz), 1.95(1H, m), 2.03(1H, ddd, J=2.2 Hz, 6.4 Hz, 14.0 Hz), 2.09(1H, ddd, J=2.1 Hz, 3.8 Hz, 15.0 Hz), 2.16(1H, dd, J=9.0 Hz, 10.8 Hz), 2.25(1H, t, J=14.3 Hz), 2.31(1H, brd, J=13.5 Hz), 2.37(1H, dt, J=6.5 Hz, 13.5 Hz), 2.92(1H, d, J=3.9 Hz), 3.08(1H, d, J=3.9 Hz), 3.39(1H, dd, J=4.6 Hz, 11.0 Hz), 3.46(1H, dd, J=2.4 Hz, 10.6 Hz).

$^{13}$C-NMR (125 MHz, CDCl$_3$) δ(ppm): 8.2(CH$_3$), 11.4(CH$_3$), 12.4(CH$_2$), 12.5(CH), 18.9(CH$_3$), 19.1(CH$_3$), 23.7(CH$_2$), 26.8(CH$_2$), 27.6(CH), 28.8(CH$_2$), 29.4(CH$_2$), 31.0(CH$_2$), 33.7(CH), 34.9(CH),

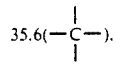

35.6(—C—), 38.1(CH$_2$), 38.4(CH$_2$), 40.1(CH$_2$), 44.5(CH$_2$), 46.5(CH), 48.1(CH),

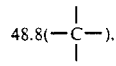

48.8(—C—), 50.6(CH$_2$), 52.2(CH), 54.3(CH),

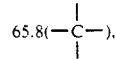

65.8(—C—), 72.2(CH), 77.4(CH), 211.8(CO)

PHARMACOLOGICAL TEST EXAMPLE 1

Result of the screening for antitumor activity of the present compound (YT-040) (in vitro inhibition of the growth of KB cells)

To each of the wells of a flat 96-well plate was added a cell suspension of KB cells at $1\times 10^3$ cells/0.1 ml of culture medium (minimal essential medium supplemented with 10% fetal calf serum). After 24-hour incubation, 100 μl of a YT-040 solution which had been prepared by dissolving YT-040 in dimethyl sulfoxide and diluting in culture medium was added to each of the culture well followed by incubation for additional 72 hours. After completion of the incubation an MTT [3-(4,5-dimethylthiazol-2-yl)-2,5-diphenyltetrazolium bromide] reagent was added followed by incubation for additional 4 hours. After completion of the incubation, culture medium was removed from wells and cells were dissolved in dimethyl sulfoxide. Subsequently, measurement was made for absorbance and ratio of the absorbance for the drug-treated group to that for the control group was determined to calculate 50%-inhibitory concentration (IC$_{50}$). IC$_{50}$ of YT-040 was 0.042 μg/ml.

PHARMACOLOGICAL TEST EXAMPLE 2

Investigation on in vivo survival-prolonging effect of YT-040 against P388 leukemia P388 leukemia cells were intraperitoneally transplanted into DBA/2 female mice at $5\times 10^5$ cells per animal.

Tumor cells were collected from ascites of the animal on day 7 of the transplantation.

A cell suspension was prepared containing $5\times 10^6$ viable cells/ml of Hank's balanced salt solution, and 0.2 ml of the cell suspension was intraperitoneally transplanted into each of CDF$_1$ female mice (7-week old) ($1\times 10^6$ cells/animal). Taking the day on which the cells were transplanted as day 0, a suspension of YT-040 in a 0.5% gum arabic-physiological saline solution was intraperitoneally administered for 5 days from day 1.

Adriamycin (ADM, Adriacin: Kyowa Hakko) was dissolved in physiological-saline solution and used as a control drug.

The result was evaluated by determining median survival time (MST) of the mouse and calculating T/C % according to the following equation:

$$T/C\,(\%) = \frac{(MST\text{ for the drug-treated group})}{(MST\text{ for the control group})} \times 100$$

The T/C was rated (+) for ≧125% and (++) for ≧175%.

The result is given in Table 1.

TABLE 1

| Sample | Dose (mg/kg) | T/C (%) | Body weight gain day 4-1 (g) |
|---|---|---|---|
| YT-040 | 1.6 | 155 | 0.7 |
|  | 6.25 | 172 | −0.5 |
|  | 25 | 76 | toxic |
| ADM | 0.8 | 159 | 0.6 |
|  | 1.6 | 191 | 0.1 |
|  | 3.13 | 194 | −0.3 |
| (MST = 9.3 days for the control) | | | |

PHARMACOLOGICAL TEST EXAMPLE 3

Investigation on in vivo survival-prolonging effect of YT-040 against L1210 leukemia L1210 leukemia cells were intraperitoneally transplanted into DBA/2 female mice at $1\times 10^5$ cells per animal. Tumor cells were collected from ascites of the animal on day 7 of the transplantation.

A cell suspension was prepared containing $5\times 10^5$ viable cells/ml of Hank's balanced salt solution, and 0.2 ml of the suspension was intraperitoneally transplanted into each of CDF$_1$ female mice (7-week old) ($1\times 10^5$ cells/animal). Taking the day on which the cells were transplanted as day 0, a suspension of YT-040 in a 0.5% gum arabic-physiological saline solution was intraperitoneally administered for 5 days from day 1.

Adriamycin (ADM, Adriacin injection: Kyowa Hakko) was dissolved in physiological saline solution and used as a control drug.

The result of evaluated by determining median survival time (MST) of the mouse and calculating T/C % according to the following equation:

$$T/C\,(\%) = \frac{(MST\text{ for the drug-treated group})}{(MST\text{ for the control group})} \times 100$$

The T/C was rated (+) for ≧125% and (++) for ≧150%.

The result is given in Table 2.

TABLE 2

| Sample | Dose (mg/kg) | T/C (%) | Body weight gain day 4-1 (g) |
|---|---|---|---|
| YT-040 | 1.6 | 220 | 0.3 |
|  | 3.13 | 209 | −0.2 |
|  | 6.25 | 124 | −0.5 |
|  | 12.5 | 92 | toxic |
| ADM | 0.4 | 127 | −0.2 |
|  | 0.8 | 176 | −0.1 |
|  | 1.6 | 209 | −0.2 |
| (MST = 9.1 days for the control) | | | |

What is claimed is:

1. A sterol compound having the formula
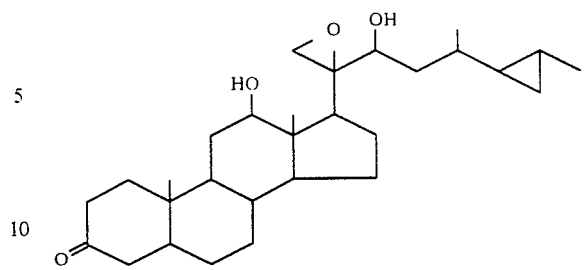
2. An antitumor pharmaceutical composition comprising a therapeutically effective amount of a compound according to claim 1 and a pharmaceutical carrier therefor.